United States Patent [19]

Diehr et al.

[11] Patent Number: 5,147,443
[45] Date of Patent: Sep. 15, 1992

[54] MICROBICIDAL AGENTS

[75] Inventors: Hans-Joachim Diehr, Wuppertal;
Karl-Heinz Kuck, Langenfeld;
Wilfried Paulus, Krefeld;
Hans-Georg Schmitt, Krefeld, all of
Fed. Rep. of Germany

[73] Assignee: Bayer Aktiengesellschaft,
Leverkusen, Fed. Rep. of Germany

[21] Appl. No.: 767,528

[22] Filed: Sep. 26, 1991

Related U.S. Application Data

[63] Continuation of Ser. No. 581,441, Sep. 11, 1990, abandoned, which is a continuation of Ser. No. 210,898, Jun. 24, 1988, abandoned.

[30] Foreign Application Priority Data

Jul. 7, 1987 [DE] Fed. Rep. of Germany ....... 3722320

[51] Int. Cl.[5] ............................................. A01N 43/82
[52] U.S. Cl. ........................................ 71/67; 514/363;
548/136; 71/90; 424/402; 424/404; 422/37;
8/490; 106/18.33
[58] Field of Search .................... 71/67, 90; 548/136;
514/363

[56] References Cited

U.S. PATENT DOCUMENTS

| | | | |
|---|---|---|---|
| 3,562,284 | 2/1971 | Newman et al. | 548/136 |
| 3,690,858 | 9/1972 | Dahle | 71/67 |
| 3,874,874 | 4/1975 | Cebalo et al. | 71/67 |
| 4,061,645 | 12/1977 | Nusslein et al. | 548/136 |
| 4,066,775 | 1/1978 | Pommer et al. | 514/363 |
| 4,314,838 | 2/1982 | Felix | 71/67 |

Primary Examiner—Carolyn Elmore
Assistant Examiner—Brian Bembenick
Attorney, Agent, or Firm—Sprung Horn Kramer & Woods

[57] ABSTRACT

The invention relates to the use of 2,5-substituted 1,3,4-thiadiazoles of the formula

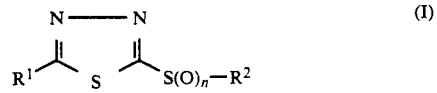

(I)

in which
$R^1$ stands for straight-chain or branched halogenoalkyl,
$R^2$ stands for straight-chain or branched alkyl and
n stands for the numbers 1 or 2, as microbicides for protecting industrial materials.

4 Claims, No Drawings

MICROBICIDAL AGENTS

This application is a continuation of application Ser. No. 581,441 filed Sep. 11, 1990, abandoned, which is a continuation of application Ser. No. 07/210,898, Jun. 24, 1988, abandoned.

The present invention relates to the use of certain 2,5-substituted 1,3,4-thiadiazoles as microbicides for protecting industrial materials.

It has been disclosed in DE-OS (German Published Specification 1,817,069 (U.S. Pat. No. 4,061,645) that certain 2,5-substituted thiadiazoles are effective fungicides against noxious fungi which are found in the soil, on seeds and on other parts of plants.

The action of these compounds against fungi pathogenic to humans has been disclosed in U.S. Pat. No. 3,562,284.

It has now been found that these 2,5-substituted 1,3,4-thiadiazoles exhibit a surprisingly high activity and an extraordinarily wide range of action against microorganisms, such as bacteria, algae, slime-producing organisms and fungi, effecting the degradation of, or a change in, industrial materials, and which are therefore extremely suitable as microbicides for protecting industrial materials.

The invention thus relates to the use of 2,5-substituted 1,3,4-thiadiazoles of the formula

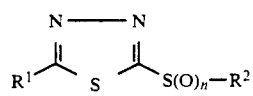

(I)

in which
R$^1$ stands for straight-chain or branched halogenoalkyl,
R$^2$ stands for straight-chain or branched alkyl and
n stands for the numbers 1 or 2,
as microbicides for protecting industrial materials.

Those compounds of the formula (I) in which n has the given meaning and
R$^1$ stands for straight-chain or branched C$_1$-C$_4$-halogenoalkyl having 1 to 9 identical or different halogen atoms and
R$^2$ stands for straight-chain or branched C$_1$-C$_8$-alkyl,
are preferably used.

Examples of C$_1$-C$_4$-halogenoalkyl radicals which may be mentioned are: dichlorofluoromethyl, chlorodifluoromethyl, trifluoromethyl, trichloromethyl, chloromethyl, dichloromethyl, 1-chloroethyl, 2-fluoromethylpropyl and 1,3-dichloro-2-methyl-propyl.

Halogenoalkyl radicals which are particularly preferred are: dichlorofluoromethyl, difluorochloromethyl, triflurormethyl, trichloromethyl, chloromethyl and dichloromethyl.

C$_1$-C$_8$-alkyl radicals which may be mentioned are: methyl, ethyl, n-propyl, iso-propyl, n-butyl, sec.-butyl, tert.-butyl, pentyl radicals, such as the n-pentyl and the neo-pentyl radical, n-hexyl, n-heptyl and the n-octyl radical.

Alkyl radicals which are particularly preferred are: methyl, ethyl, n-propyl and iso-propyl.

Examples of representatives of the 2,5-substituted 1,3,4-thiadiazoles of the formula (I) to be used according to the invention which may be mentioned are:

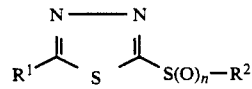

(I)

TABLE 1

| R$^1$ | n | R$^2$ | Melting point (°C.) Refractive index |
|---|---|---|---|
| CF$_3$ | 2 | CH$_3$ | 86 |
| CCl$_3$ | 1 | CH$_3$ | 109 |
| CCl$_3$ | 2 | CH$_3$ | 118 |
| CCl$_2$F | 1 | CH$_3$ | 56–57 |
| CCl$_2$F | 2 | CH$_3$ | 57 |
| CClF$_2$ | 2 | CH$_3$ | 60 |
| CH$_2$Cl | 2 | CH$_3$ | 57 |
| CH$_2$Cl | 1 | CH$_3$ | n$_D^{20}$ = 1.5948 |
| CCl$_3$ | 2 | C$_3$H$_7$-n | 80 |
| CHCl$_2$ | 2 | CH$_3$ | 79 |
| CHCl$_2$ | 1 | CH$_3$ | 89 |
| —CH—CH$_3$ \| Cl | 2 | CH$_3$ | n$_D^{20}$ = 1.5455 |
| —CH—CH$_3$ \| Cl | 1 | CH$_3$ | 83 |
| CCl$_3$ | 2 | C$_8$H$_{17}$-n | 109 |
| CCl$_3$ | 2 | C$_2$H$_5$ | 68 |
| CH$_3$ \| —C—CH$_2$F \| CH$_3$ | 2 | CH$_3$ | n$_D^{20}$ = 1.5086 |
| CH$_2$Cl \| —C—CH$_3$ \| CH$_2$Cl | 2 | CH$_3$ | n$_D^{20}$ = 1.522 |

The preparation of the 1,3,4-thiadiazoles of the formula I to be used according to the invention is described in U.S. Pat. Nos. 4,005,213 and 3,562,284, and a process for the preparation of the 5-mercapto-1,3,4-thiadiazoles required as starting compounds is described, for example, in U.S. Pat. No. 3,562,284.

The industrial materials to be protected according to the invention are non-living materials, which have been prepared for industrial use. Industrial materials which are to be protected from microbial change or destruction by the active compounds to be used according to the invention can be, for example, adhesives, glues, paper and cardboard, textiles, leather, wood, paints and articles made of plastics, cooling lubricants and other materials which can be attacked or degraded by microorganisms. Within the scope of the materials to be protected parts of production plants may also be mentioned, for example coolant circuits, which may be impaired by the multiplication of microorganisms. Industrial materials which may be mentioned within the scope of the present invention are preferably adhesives, glues, papers and cardboards, leather, wood, paints, cooling lubricants and liquids for heat transfer.

Examples which may be mentioned of microorganisms which can effect a degradation of or a change in the industrial materials and which are therefore combated in the protection of materials are bacteria, fungi, yeasts, algae and slime-producing organisms. The active compounds according to the invention preferably act against fungi, in particular moulds, wood-discolouring and wood-destroying fungi (Basidiomycetes), and against slime-producing organisms and algae.

For example, microorganisms of the following genera may be mentioned: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeruginosa*, Staphylococcus, such as *Staphylococcus aureus*.

Depending on the field of application, an active compound according to the invention may be converted into the customary formulations, such as solutions, emulsions, suspensions, powders, pastes and granules.

These can be produced in a manner known per se, for example by mixing the active compounds with an extender, which consists of a liquid solvent and/or solid carriers, if appropriate with the use of surface-active agents, such as emulsifying agents and/or dispersing agents, in the case of water being used as the extender, it being possible, if appropriate, for organic solvents, such as alcohols, to be used as auxiliary substances.

Liquid solvents for the active compounds, can be, for example, water, alcohols, such as lower aliphatic alcohols, preferably ethanol or isopropanol, or benzyl alcohol, ketones, such as acetone or methyl ethyl ketone, liquid hydrocarbons, such as petroleum fractions, and halogenated hydrocarbons, such as 1,2-dichloroethane.

Microbicidal agents generally contain the active compounds to be used according to the invention in an amount of 1 to 95% by weight, preferably of 10 to 75% by weight, relative to the total weight of the agent.

The application concentrations of the active compounds to be used according to the invention depend on the species and on the occurrence of the microorganisms to be combated, and on the composition of the material to be protected. The optimum application rate can be determined by test series. In general, the application concentrations are in the range of 0.001 to 5% by weight, preferably 0.05 to 1.0% by weight, relative to the material to be protected.

The active compounds to be used according to the invention can also be present as a mixture with other known active compounds. The following active compounds may be mentioned as examples: benzyl alcohol mono(poly) hemiformal and other compounds which release formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzthiazole, organo-tin compounds, methylene bisthiocyanate, phenol derivatives, such as 2-phenylphenol, (2,2'-dihydroxy-5,5'-dichloro)-diphenylmethane, 3-methyl-4-chlorophenol and 2-thiocyanatomethylthiobenzthiazole.

The 1,3,4-thiadiazoles used in the following examples had been obtained as follows:

Stage 1 (preparation of the mercapto compounds)

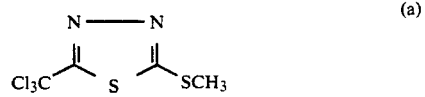
(a)

36.6 g (0.3 mol) of methyl dithiocarbazate were dissolved in 100 ml of diethylene glycol dimethyl ether and 23.7 g (0.3 mol) of pyridine, and the batch was cooled to 0° C. to 5° C. 54.6 g (0.3 mol) of trichloroacetyl chloride were added dropwise at this temperature. The mixture was then stirred for a further 30 minutes at room temperature, 70 ml of concentrated sulphuric acid were then added dropwise at 0° C. to 10° C., and the mixture was finally stirred for 12 hours at room temperature. The reaction mixture was poured into ice water; the aqueous mixture was extracted with toluene. The combined toluene extracts were freed from the toluene in vacuo. Incipient distillation of the residue was carried out in a steam-jet apparatus at a bath temperature of 50°-60° C.

Yield: 69.6 g (=93.5% of theory) of 5-trichloromethyl-2-methylmercapto-1,3,4-thiadiazole in the form of a slowly crystallizing dark oil.

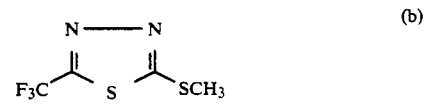
(b)

Firstly 211 g (1.54 mol) of phosphorus trichloride and then 114 g (1 mol) of trifluoroacetic acid in 90 ml of toluene were added dropwise to a solution of 128 g (1 mol) of methyl dithiocarbazate (96% strength) in 260 ml of toluene and 87 g (1.1 mol) of pyridine at −5° C. to 0° C. After warming to room temperature, the reaction mixture was stirred for a further 12 hours at this temperature, and 100 ml of concentrated sulphuric acid were then added at room temperature, with cooling. The mixture was then heated for 2 hours to 45°-55° C., cooled, and poured into ice water. The aqueous mixture was extracted repeatedly with toluene. The organic phase was dried and freed from the toluene. Yield: 169.9 g (97% strength) (=82.4% of theory) of 5-trifluoromethyl-2-methylmercapto-1,3,4-thiadiazole in the form of a yellowish oil (b.p. 44° C./0.67 mbar).

Stage 2a) (Preparation of the sulphones)

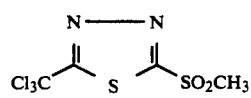

25.5 g (0.12 mol) of 2-trichloromethyl-5-methylmercapto-1,3,4-thiadiazole and 1 g of sodium tungstate were dissolved in 100 ml of formic acid, and 50 ml of hydrogen peroxide were added dropwise to the solution at room temperature. The mixture was warmed to 70° C., stirred at this temperature for 15 minutes, and then cooled to room temperature. Water was then added to the reaction mixture, and extraction was carried out with dichloromethane. The organic phases were dried over magnesium sulphate and concentrated.

Yield: 23.3 g (69% of theory) of 2-trichloromethyl-5-methylsulphonyl-1,3,4-thiadiazole MP.: 118° C.

Analogously, 2-trifluoromethyl-5-methylsulphonyl-1,3,4-thiadiazole was obtained from 2-trifluoromethyl-5-methylmercapto-1,3,4-thiadiazole; m.p.; 86° C.

Stage 2b (preparation of the sulphinyl compound)

The solution of 17.3 g (0.1 mol) of m-chloroperbenzoic acid in 150 ml of dichloromethane was added dropwise to the solution of 25 g (0.1 mol) of 2-trichloromethyl-5-methylmercapto-1,3,4-thiadiazole (from stage 1a) in 100 ml of dichloromethane at −60° C. The reaction mixture was allowed to warm to room temperature and was stirred for a further hour at this temperature. The batch was poured into bicarbonate solution and the organic phase was separated off, washed, dried over sodium sulphate and freed from the solvent in vacuo.

The residue was recrystallized from isopropanol.
Yield: 18.1 g (68% of theory) of 2-trichloromethyl-5-methylsulphinyl-1,3,4-thiadiazole; MP.: 109° C.

USE EXAMPLES

Example A

For determining the activity against fungi, the minimum inhibitory concentrations (MIC) of active compounds to be used according to the invention are determined:

Active compounds according to the invention are added to an agar prepared from brewer's wort and peptone in concentrations of 0.1 mg/l to 5,000 mg/l. After the agar has solidified, it is contaminated with pure cultures of the test organisms listed in the table. After storing for 2 weeks at 28° C. and a relative atmospheric humidity of 60 to 70%, the MIC is determined.

The MIC is the lowest concentration of active compound at which no growth of any kind takes place for the species of microorganism used, and is given in the following table.

TABLE A

MICs in mg/l in the action against fungi of 1,3,4-thiadiazoles to be used according to the invention

| Test organism | Active compound | | |
|---|---|---|---|
| | $F_3C{-}\underset{S}{\overset{N-N}{\triangle}}{-}SO_2CH_3$ | $Cl_3C{-}\underset{S}{\overset{N-N}{\triangle}}{-}S(O){-}CH_3$ | $Cl_3C{-}\underset{S}{\overset{N-N}{\triangle}}{-}SO{-}CH_3$ |
| *Alternaria tenuis* | 15 | 5 | 10 |
| *Aspergillus niger* | 20 | 50 | 20 |
| *Aureobasidium pullulans* | 10 | 5 | 15 |
| *Chaetomium globosum* | 10 | 20 | 10 |
| *Cladosporium cladosporioides* | 5 | 5 | 2 |
| *Lentinus tigrinus* | 2 | 2 | 2 |
| *Penicillium glaucum* | 20 | 20 | 10 |
| *Sclerophoma pityophila* | 5 | 5 | 10 |
| *Trichoderma viride* | 200 | 100 | 200 |

Example B

Action Against Bacteria

Active compounds to be used according to the invention are added to an agar containing bouillon as the nutrient medium in concentrations of 1 to 5,000 ppm. The nutrient medium is then infected in each case with the test organisms listed in Table B, and the infected medium is kept at 28° C. and 60 to 70% of relative atmospheric humidity for 2 weeks.

The MIC is the lowest concentration of active compound at which no growth of any kind takes place for the species of microorganism used. The MIC values are listed in Table B.

TABLE B

MIC values given in mg/l for the action against bacteria of the active compounds listed below.

| Test organism | Active compound | |
|---|---|---|
| | $F_3C{-}\underset{S}{\overset{N-N}{\triangle}}{-}SO_2CH_3$ | $Cl_3C{-}\underset{S}{\overset{N-N}{\triangle}}{-}S(O){-}CH_3$ |
| *Escherichia coli* | 200 | 20 |
| *Staphylococcus aureus* | 200 | 35 |
| *Pseudomonas aeruginosa* | 200 | 500 |
| *Pseudomonas fluorescens* | 200 | 200 |
| *Bacillus substilis* | 500 | — |
| *Bacterium punctatum* | 750 | — |
| *Proteus mirabilis* | 100 | 20 |

Example C

Action Against Slime-Producing Organisms

Compounds to be used according to the invention are applied, dissolved in a little acetone, in concentrations of 0.1 to 100 mg/l in each case in Allen's nutrient solution (Arch. Mikrobiol. 17, 34–53 (1952)), which contains 0.2 g of ammonium chloride, 4.0 g of sodium nitrate, 1.0 g of dipotassium hydrogenphosphate, 0.2 g of calcium chloride, 2.05 g of magnesium sulphate, 0.02 g of iron chloride and 1% of caprolactam in 4 l of sterile water. Just before application, the nutrient solution is infected with slime-producing organisms (approx. $10^6$ germs/ml), which have been isolated from spinning water circuits used in polyamide production.

After 3 weeks of incubation at room temperature, nutrient solutions which have the minimum inhibitory concentration (MIC) or higher concentrations of active compound are still completely clear, i.e., the considerable multiplication of the microorganisms and formation of slime which can be observed after 3 to 4 days in nutrient solutions devoid of active compound does not occur.

TABLE C

MIC value on mg/l for the action on slime-producing organisms of the substances listed below

| Example No. | MIC in mg/l |
|---|---|
| $Cl_3C$—[N=N thiadiazole]—$S(O)$—$CH_3$ | 0.3 |
| $Cl_3C$—[N=N thiadiazole]—$S(O)$—$CH_3$ | 0.5 |
| $F_3C$—[N=N thiadiazole]—$SO_2CH_3$ | 0.75 |

Example D

A mixed culture of green, blue-green and brown algae and diatoms (*Stichococcus bacillaris* Naegali, *Euglena gracilis* Klebs, *Chlorella pyrenoidosa* Chick, *Phormidium foveolarum* Gomont, *Oscillatoria geminata* Meneghini and *Phaedodactylum tricornutum* Bohlin) is added to Allen's nutrient solution (Arch. Mikrobiol. 17, 34-53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride per 4 l of sterile water, while bubbling in air.

After 2 weeks, the nutrient solution is a deep green-blue colour, caused by intensive growth of algae. After the addition of active compounds to be used according to the invention, the dieing-off of algae can be recognized by the decolouring of the nutrient solution.

TABLE D

Algae-fatal concentrations (mg/l) of the substances listed below

| Example No. | fatal concentration in mg/l |
|---|---|
| $Cl_3C$—[N=N thiadiazole]—$S(O)$—$CH_3$ | 100 |
| $Cl_3C$—[N=N thiadiazole]—$S(O)$—$CH_3$ | 30 |
| $F_3C$—[N=N thiadiazole]—$SO_2CH_3$ | 75 |

Example E

Test for Mould-Resistance of Coatings

The test is carried out in accordance with Report 219 of Defense Standards Laboratories Marigyrnong/Australia as follows:

The paint to be tested is brushed on both sides of a suitable base.

In order to obtain results similar to those achieved in practice, some of the test pieces are treated with a warm stream of fresh air before testing for mould resistance (7 days; 40° C.).

The test pieces thus prepared are put onto an agar nutrient medium. Test piece and nutrient medium are contaminated with fungal spores. Assessment is carried out after 1 to 3 weeks of storage at 29°±1° C. and 80-90% of relative atmospheric humidity. The coating is permanently mould-resistant if the test piece remains free from fungus or if, at the most, slight infestation at the edges can be observed.

For contamination, fungal spores of the following nine moulds, which are known as coating destructants or are frequently found on coatings, are used:
1. *Alternaria tenuis*
2. *Aspergillus flavus*
3. *Aspergillus niger*
4. *Aspergillus ustus*
5. *Cladosporium herbarum*
6. *Paecilomyces variotii*
7. *Penicillium citrinum*
8. *Aureobasidium pullulans*
9. *Stachybotrys atra* Corda A dispersion paint based on PVAc containing 0.5% of active compound (7) or 0.5% of active compound (8) relative to the total solids content gives mould-resistant coatings in accordance with the test as described above.

Using the commercially available paint fungicide tetramethylthiuram disulphide (TMTD) in the same dispersion paint, this effect is achieved only after incorporation of at least 3% TMTD relative to the total solid substance content.

Paints and coatings containing TMTD discolour when they come into contact with traces of heavy metals. Coatings and paints containing the active compounds according to the invention do not discolour.

What is claimed is:

1. A method for protecting industrial materials from attach by algae which method comprises contacting the industrial material with an effective amount of a 2,5-substituted 1,3,4-thiadiazole of the formula

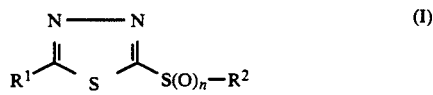

in which
R$^1$ is a straight-chain or branched halogenalkyl,
R$^2$ is a straight-chain or branched alkyl and
n is 1 or 2.

2. The method of claim 1, wherein in formula (I),
R$^1$ is a straight-chain or branched $C_1$-$C_4$-halogenalkyl having 1 to 9 identical or different halogen atoms and
R$^2$ is a straight-chain or branched $C_1$-$C_8$-alkyl.

3. The method of claim 1, wherein the industrial material is an adhesive, a glue, paper, cardboard, textile, leather, wood or paint.
4. The method of claim 1, wherein the 2,5-substituted 1,3,4-thiadiazole is of the formula
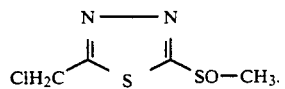
* * * * *

UNITED STATES PATENT AND TRADEMARK OFFICE
CERTIFICATE OF CORRECTION

PATENT NO. : 5,147,443
DATED : September 15, 1992
INVENTOR(S) : Hans-Joachim Diehr, et al.

It is certified that error appears in the above-indentified patent and that said Letters Patent is hereby corrected as shown below:

Column 8, line 51        Delete "attach" and substitute -- attack --

Column 8, line 61        Delete "halogenalkyl" and substitute -- halogenoalkyl --

Column 8, lines 65-66    Delete "halogenalkyl" and substitute -- halogenoalkyl --

Signed and Sealed this

Nineteenth Day of April, 1994

Attest:

BRUCE LEHMAN

*Attesting Officer*        Commissioner of Patents and Trademarks